US012597139B2

(12) United States Patent
Goshen

(10) Patent No.: US 12,597,139 B2
(45) Date of Patent: Apr. 7, 2026

(54) CONTROLLING AN ALERT SIGNAL FOR SPECTRAL COMPUTED TOMOGRAPHY IMAGING

(71) Applicant: KONINKLIJKE PHILIPS N.V., Eindhoven (NL)

(72) Inventor: Liran Goshen, Perdes-Hanna (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 303 days.

(21) Appl. No.: 18/569,546

(22) PCT Filed: Jun. 9, 2022

(86) PCT No.: PCT/EP2022/065616
§ 371 (c)(1),
(2) Date: Dec. 12, 2023

(87) PCT Pub. No.: WO2022/263261
PCT Pub. Date: Dec. 22, 2022

(65) Prior Publication Data
US 2024/0273725 A1      Aug. 15, 2024

(30) Foreign Application Priority Data

Jun. 17, 2021     (EP) ..................................... 21180119

(51) Int. Cl.
*G06T 7/00*          (2017.01)
*A61B 6/00*          (2024.01)
(Continued)

(52) U.S. Cl.
CPC ............ *G06T 7/0014* (2013.01); *A61B 6/032* (2013.01); *A61B 6/461* (2013.01); *A61B 6/5205* (2013.01);
(Continued)

(58) Field of Classification Search
CPC ........ G06N 3/00; G06N 3/0464; A61B 6/032; A61B 6/4241; A61B 6/461; A61B 6/482;
(Continued)

(56) References Cited

U.S. PATENT DOCUMENTS

| | | | |
|---|---|---|---|
| 7,968,853 | B2 | 6/2011 | Altman |
| 8,938,110 | B2 | 1/2015 | Goshen |

(Continued)

FOREIGN PATENT DOCUMENTS

| | | | |
|---|---|---|---|
| EP | | 3467771 A1 | 10/2019 |
| WO | WO2019141527 A1 | | 7/2019 |
| WO | WO2019149711 A1 | | 8/2019 |

OTHER PUBLICATIONS

PCT International Search Report, International application No. PCT/EP2022/065616, Sep. 15, 2022.

(Continued)

*Primary Examiner* — Vu Le
*Assistant Examiner* — Jessica Yifang Lin
(74) *Attorney, Agent, or Firm* — Larry Liberchuk

(57) ABSTRACT

A mechanism for identifying potential areas of clinical relevance that are not readily visible in non-spectral CT image data. The non-spectral CT image data is processed using a machine-learning method to produce predicted spectral CT image data. The predicted spectral CT image data is compared to (actual) spectral CT image data to identify any differences between the two. Any identified differences are used to control an alert signal, for instance, to draw a clinician or other user's attention to possible areas of clinical relevance that are not readily visible in the non-spectral CT image data.

15 Claims, 5 Drawing Sheets

(51) Int. Cl.
 *A61B 6/03* (2006.01)
 *A61B 6/46* (2024.01)
(52) U.S. Cl.
 CPC ...... *A61B 6/54* (2013.01); *G06T 2207/10081*
 (2013.01); *G06T 2207/20081* (2013.01); *G06T*
 *2207/20224* (2013.01)
(58) Field of Classification Search
 CPC ....... A61B 6/5205; A61B 6/54; A61B 8/5223;
 A61B 8/5292; G06T 2207/10081; G06T
 2207/20081; G06T 2207/20224; G06T
 7/0014
 See application file for complete search history.

(56) References Cited

U.S. PATENT DOCUMENTS

| | | | |
|---|---|---|---|
| 9,980,686 B2 | 5/2018 | Proksa | |
| 2018/0137244 A1 | 5/2018 | Sorenson | |
| 2018/0276802 A1* | 9/2018 | Lichy | G06T 5/92 |
| 2019/0021677 A1 | 1/2019 | Grbic | |
| 2020/0372651 A1* | 11/2020 | Nye | G16H 50/20 |
| 2021/0059625 A1 | 3/2021 | Bai | |
| 2021/0065410 A1 | 3/2021 | Goshen | |

OTHER PUBLICATIONS

Johnson T. et al., "Dual Energy CT in Clinical Practice", Medical Physics, vol. 38, No. 11, pp. 6346-6346, Nov. 2011.
Goshen L. et al., "An Iodine-Calcium Separation Analysis and Virtually Non-Contrasted Image Generation Obtained with Single Source Dual Energy MDCT", 2008 IEEE Nuclear Science Symposium Conference Record, pp. 3868-3870, Oct. 2008.
Sosna, J. et al., "Virtual Nonenhanced Abdominal Dual-Energy MDCT: Analysis of Image Characteristics", World Journal of Radiology, 4(4), pp. 167-173, 2012.
Carmi, R. et al., "A Unique Noncathartic CT Colonography Approach by Using Two-Layer Dual-Energy MDCT and a Special Algorithmic Colon Cleansing Method", 2008 IEEE Nuclear Science Symposium Conference Record, pp. 4780-4783, Oct. 2008.
Carmi, R. et al., "Arterial Double-Contrast Dual-Energy MDCT: In-Vivo Rabbit Atherosclerosis with Iodinated Nanoparticles and Gadolinium Agents", Medical Imaging 2010: Biomedical Applications in Molecular, Structural, and Functional Imaging, vol. 7626, p. 76261G, International Society for Optics and Photonics, Mar. 2010.
Pinto, A. et al., "Spectrum of Diagnostic Errors in Radiology", World Journal of Radiology 2.10 (2010): 377-383, PMC. Web. Feb. 13, 2017.
Lee, C.S. et al., "Cognitive and System Factors Contributing to Diagnostic Errors in Radiology", American Journal of Roentgenology 201.3, pp. 611-617, 2013.
Berlin, L. et al., "Accuracy of Diagnostic Procedures: Has it Improved Over the Past Five Decades?", American Journal of Roentgenology, 188.5, pp. 1173-1178, 2007.
Berlin, L. et al., "Malpractice and Radiologists in Cook County, IL: Trends in 20 Years of Litigation", American Journal of Roentgenology (AJR), 1995, vol. 165, pp. 781-788, 1995.
Anderson, M. B. et al., "Impact of Spectral Body Imaging in Patients Suspected for Occult Cancer: A Prospective Study of 503 Patients", European Radiology, vol. 30, Issue 10, pp. 5539-5550, 2020.
Long, J. et al., "Fully Convolutional Networks for Semantic Segmentation", Proceedings of the IEEE Conference on Computer Vision and Pattern Recognition. 2015.
Olaf, R. et al., "U-Net: Convolutional Networks for Biomedical Image Segmentation", Medical Image Computing and Computer-Assisted Intervention (MICCAI), Springer, LNCS, vol. 9351, pp. 234-241, 2015.
Chen, A. et al., "Detection of Gallbladder Stones by Dual-Energy Spectral Computed Tomography Imaging", World Journal of Gastroenterol, 21(34):9993-9998, 2015.

* cited by examiner

510

525

520

CONTROLLING AN ALERT SIGNAL FOR SPECTRAL COMPUTED TOMOGRAPHY IMAGING

FIELD OF THE INVENTION

The present invention relates to the field of computed tomography (CT) imaging, and in particular to the field of spectral computed tomography imaging.

BACKGROUND OF THE INVENTION

Computed tomography (CT) imaging ("conventional CT") is a widely used and known approach for imaging a subject. Spectral computed tomography (CT) imaging is an imaging modality that extends the capabilities of conventional CT.

Dual-energy (DE) CT is one specific configuration of spectral CT that utilizes two attenuation values acquired simultaneously at two photon energies. These attention values can be used to solve the photoelectric and Compton contribution that consists of the mass attenuation coefficient of a material. It is therefore possible to identify an unknown material by its value of photoelectric and Compton contribution. This imaging modality works especially well in materials, such as iodine, that have k-edge energy close to the mean value of a diagnostic energy range. Because any two linearly independent sums of two basis functions span the entire attenuation coefficient space, any material can be represented by a linear combination of two other materials, so called basis materials, such as water and iodine.

Recent technical advances have developed several approaches for performing dual-energy CT accusation such as dual-source, fast kVp switching, and dual-layer detector configurations.

Quantitative imaging has been of increasing interest to the medical imaging community. Spectral CT modalities supports this trend, as the additional spectral information improves the quantitative information that can be measured about the scanned object and its material composition.

Diagnostic radiology aims to perform complete detection of all findings or abnormalities during an imaging examination, and perform accurate assessment and/or diagnosis of the same. However, error rates during radiologic examinations are relatively high. Overall, approximately 30% of abnormal radiographic studies are missed, and approximately 4% of radiologic interpretations rendered by radiologists in daily practice contain errors. As a result, there is a clear and increasing demand to improve the diagnostic reading environment and tools for aiding a clinician to review and assess CT images.

SUMMARY OF THE INVENTION

The invention is defined by the claims.

According to examples in accordance with an aspect of the invention, there is provided a computer-implemented method of controlling an alert signal responsive to differences between spectral CT image data and predicted spectral CT image data.

The computer-implemented method comprises: obtaining non-spectral CT image data and spectral CT image data, each representing a same region of interest of the subject; processing the non-spectral CT image data, using a machine-learning algorithm, to produce predicted spectral CT image data, the predicted spectral CT image data being a prediction of the spectral CT image data derived from the non-spectral CT image data; processing the spectral CT image data and the predicted spectral CT image data to identify any differences between the spectral CT image data and the predicted spectral CT image data; and controlling an alert signal responsive to any identified differences.

The present disclosure proposes an approach for generating an alert signal that indicates whether there is a potential anatomical feature or abnormality that cannot be clearly seen in non-spectral CT image data, but may still have some diagnostic importance. Embodiments are based on the realization that differences between "true" spectral CT image data and predicted spectral CT image data (generated using non-spectral CT image data) represent anatomical features or abnormalities that cannot be readily identified in the original non-spectral CT image data. In other words, a difference effectively represents a measure of imperceptibility of a particular (anatomical) feature of potential clinical relevance.

By generating an alert signal responsive to such differences, this information can be used (for instance) to alert a clinician as to a possible presence and/or position of a potential anatomical feature or abnormality not clearly visible (to the human eye) in the non-spectral CT image data.

Differences between the spectral CT image data and the predicted CT image data may thereby effectively represent anatomical features that are identifiable in the spectral CT image data, but which are not identifiable in the predicted CT spectral CT image data and/or the non-spectral CT image data.

A further advantage of the proposed approach is that the machine-learning algorithm does not require user-annotated training data. Thus, an unsupervised learning approach can be used, which significantly increases an available amount of training data and reduces professional and/or clinician time for annotating the training data. In this way, accurate identification of potentially clinically relevant areas can be achieved without the need for a machine-learning method that makes use of a supervised learning technique.

In some examples, the spectral CT image data comprises a set of one or more spectral CT images; the predicted CT image data comprises a respective set of one or more predicted spectral CT images, each predicted spectral CT image corresponding to a respective spectral CT image; and the step of identifying any differences between the spectral CT image data and the predicted CT image data comprises, for each spectral CT image, identifying any differences between the spectral CT image and the corresponding predicted spectral CT image.

The step of identifying any differences between the spectral CT image and the corresponding predicted spectral CT image may comprise processing the spectral CT image and the corresponding predicted spectral CT image using one or more functions to produce a difference image that identifies a presence and position of differences between the spectral CT image and the corresponding predicted spectral CT image.

The identified presence and position of differences may be used, for instance, to alert a clinician as to the presence of potential anatomical features or abnormalities that might otherwise be overlooked by the clinician. In particular the position of differences may be used to identify a most relevant spectral CT image for review by the clinician.

Optionally, the step of processing the spectral CT image and the corresponding predicted spectral CT image comprises, for each pixel/voxel of the spectral CT image, determining a difference between the pixel/voxel of the spectral CT image and the corresponding pixel/voxel of the predicted spectral CT image.

In some examples, the step of processing the spectral CT image and the corresponding predicted spectral CT image comprises: performing a standard deviation filtering function on the spectral CT image to produce a standard deviation spectral CT image having a same resolution as the spectral CT image; and for each pixel/voxel of the spectral CT image, dividing the determined difference by a value derived from the value of the corresponding pixel/voxel of the standard deviation spectral CT image.

The value derived from the value of the corresponding pixel/voxel of the standard deviation spectral CT image may be equal to the value of the corresponding pixel/voxel of the standard deviation spectral CT image or equal to the value of the corresponding pixel/voxel of the standard deviation spectral CT image plus a predetermined value. This latter embodiment helps to reduce a likelihood of dividing by zero, e.g. reduce the likelihood of a divide-by-zero error occurring. The predetermined value may be very small (e.g. <0.01 or less than 1% of a maximum possible value for a pixel of a spectral CT image).

In at least one embodiment. the step of processing the spectral CT image and the corresponding predicted CT image comprises processing the spectral CT image and the corresponding predicted CT image using a cross-correlation or mutual information function.

The step of controlling the alert signal may comprise controlling the alert signal responsive to the presence and position of differences between the spectral CT image and the corresponding predicted CT image in any difference map.

The set of one or more spectral CT images may comprise a plurality of spectral CT images. In some examples, the method further comprises identifying, based on any identified differences, one or more of the plurality of spectral CT images that contains a representation of the cause of the identified difference.

The method may further comprise controlling a user-perceptible output responsive to the alert signal.

The computer implemented method may further comprising obtaining input parameter data, the input parameter data defining one or more parameters of the acquisition protocol used, by a CT imaging system, in acquiring the non-spectral CT image data and/or the spectral CT image data, preferably wherein the step of processing the non-spectral CT image data comprises processing the non-spectral CT image data and the input parameter data using the machine-learning algorithm to produce the predicted spectral CT image data.

In other words, the machine-learning algorithm may receive as input (features) the non-spectral CT image data and the input parameter data.

In at least one example, the computer-implemented method further comprises obtaining reconstruction parameter data, the reconstruction parameter data defining one or more parameters of the reconstruction protocol used, by a CT imaging system, to process raw CT data to produce the non-spectral CT image data and/or the spectral CT image data, preferably wherein the step of processing the non-spectral CT image data comprises processing the non-spectral CT image data and the reconstruction parameter data using the machine-learning algorithm to produce the predicted spectral CT image data.

Of course, in some embodiments, the step of processing the non-spectral CT image data comprises processing the non-spectral CT image data, the input parameter data and the reconstruction parameter data (using the machine-learning algorithm) to produce the predicted spectral CT image data. In other words, the machine-learning algorithm may receive as input (features) the non-spectral CT image data, the input parameter data and/or the reconstruction parameter data.

The method may further comprise obtaining subject data, the subject data defining one or more parameters of the subject, wherein the step of processing the non-spectral CT image data comprises processing the non-spectral CT image data and the subject data using the machine-learning algorithm to produce the predicted spectral CT image data.

Of course, it will be appreciated that the step of processing the non-spectral CT image data comprises processing the non-spectral CT image data and one or more of: the input parameter data. the reconstruction parameter data and/or the subject data (using the machine-learning algorithm) to produce the predicted spectral CT image data. In other words, the machine-learning algorithm may receive as input (features) the non-spectral CT image data and one or more of: the input parameter data, the reconstruction parameter data and/or the subject-data.

There is also proposed a computer program product comprising computer program code means which, when executed on a computing device having a processing system, cause the processing system to perform all of the steps of the method as herein described. The computer program product may be formed on a (non-transitory) storage medium.

There is also proposed a processing system for controlling an alert signal responsive to differences between spectral CT image data and predicted spectral CT image data.

The processing system is configured to: obtain non-spectral CT image data and spectral CT image data, each representing a same region of interest of the subject; process the non-spectral CT image data, using a machine-learning algorithm, to produce predicted spectral CT image data, the predicted spectral CT image data being a prediction of the spectral CT image data derived from the non-spectral CT image data; process the spectral CT image data and the predicted spectral CT image data to identify any differences between the spectral CT image data and the predicted spectral CT image data; and control an alert signal responsive to any identified differences.

The processing system may obtain the non-spectral and spectral CT image data at an input interface. In particular examples, the processing system may obtain the non-spectral and spectral CT image data from a memory/storage unit and/or a CT imaging system (that generates the CT image data).

The processing system may be configured to output, e.g. at an output interface, the alert signal to another system. As one example, the processing system may be configured to control a user interface using the alert signal to thereby control a user-perceptible output responsive to the alert signal.

There is also proposed a system comprising the processing system and the user interface.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
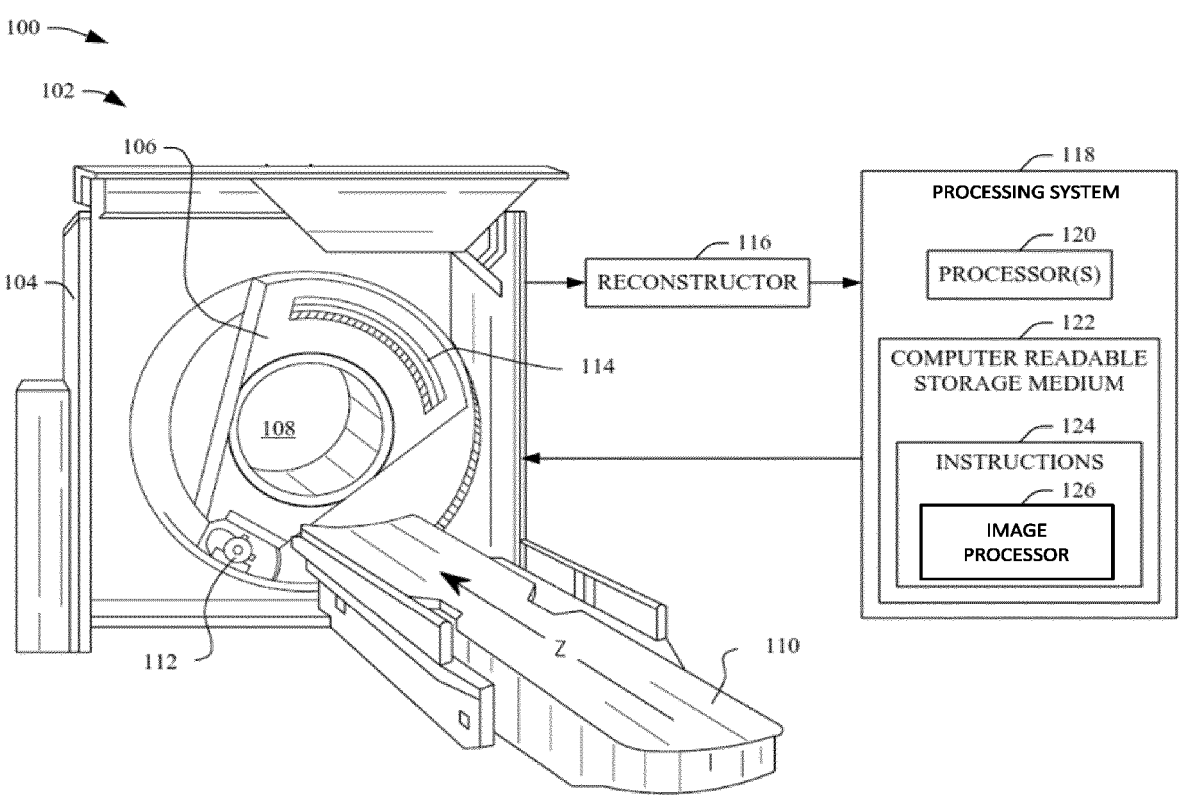
FIG. 1 illustrates a system comprising a processing system according to an embodiment.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features. aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a mechanism for identifying potential areas of clinical relevance that are not readily visible in non-spectral CT image data. The non-spectral CT image data is processed using a machine-learning method to produce predicted spectral CT image data. The predicted spectral CT image data is compared to (actual) spectral CT image data to identify any differences between the two. Any identified differences are used to control an alert signal, for instance, to draw a clinician or other user's attention to possible areas of clinical relevance that are not readily visible in the non-spectral CT image data.

The present disclosure is based on the realization that features that are not readily visible in non-spectral CT image data will not be accurately generated in a prediction of spectral CT image data from the non-spectral CT image data. This facilitates identification of missing features or areas of potential clinical relevance in the non-spectral CT image data. By using a machine-learning method to produce predicted spectral CT image data (e.g. rather than attempting to directly detect potentially missing features) a non-supervised training technique can be used to train the machine-learning network, significantly reducing a professional input required and/or significantly increasing an amount of available data for training the machine-learning method.

Embodiments of the invention may be employed in any CT imaging environment, e.g. for use in clinical environments. In particular, embodiments may be employed to aid radiographers or other clinicians in assessing the condition of a patient, by drawing the clinician's attention to potentially clinically relevant areas that might otherwise have been overlooked.

FIG. 1 schematically illustrates a system 100 including an imaging system 102 such as a CT scanner configured for conventional CT imaging and spectral (multi-energy) imaging. The imaging system 102 includes a generally stationary portion 104 and a rotating portion 106, which is rotatably supported by the stationary portion 104 and rotates around an examination region 108 about a z-axis. A subject support 110, such as a couch, supports an object or subject in the examination region 108.

A radiation source 112, such as an x-ray tube, is rotatably supported by the rotating portion 106, rotates with the rotating portion 106, and emits radiation that traverses the examination region 108.

To facilitate spectral imaging, in one instance, the radiation source 112 includes a single broad spectrum x-ray tube. In another instance, the radiation source 112 includes a single x-ray tube configured to switch between at least two different emission voltages (e.g., 80 kVp and 140 kVp) during scanning. In yet another instance, the radiation source 112 includes two or more x-ray tubes configured to emit radiation having different mean spectra. In still another instance, the radiation source 112 includes a combination thereof.

A radiation sensitive detector array 114 subtends an angular arc opposite the radiation source 112 across the examination region 108. The radiation sensitive detector array 114 detects radiation traversing the examination region 108 and generates an electrical signal(s) (projection data) indicative thereof.

To facilitate spectral imaging, where the radiation source 112 includes a single broad spectrum x-ray tube, the radiation sensitive detector array 112 includes energy-resolving detectors (e.g., direct conversion photon counting detectors, at least two sets of scintillators with different spectral sensitivities (multi-layer), etc.). With kVp switching and multi-tube configurations, the detector array 114 can include single layer detectors, direct conversion photon counting detectors, and/or multi-layer detectors. The direct conversion photon counting detectors may include a conversion material such as CdTe, CdZnTe, Si, Ge, GaAs, or other direct conversion material. An example of multi-layer detector includes a double decker detector such as the double decker detector described in U.S. Pat. No. 7,968,853 B2, filed Apr. 10. 2006, and entitled "Double Decker Detector for Spectral CT," the entirety of which is incorporated herein by reference.

A reconstructor 116 receives projection data (and/or spectral projection data) from the detector array 114 and reconstructs non-spectral CT image data and spectral volumetric image data such as sCCTA image data, a high-energy image, a low energy image, a photoelectric image, a Compton scatter image, an iodine image, a calcium image, a virtual non-contrast image, a bone image, a soft tissue image, and/or other basis material image. The reconstructor 116 is also able to reconstruct non-spectral volumetric data, e.g., by combining spectral projection data and/or spectral volumetric image data or by processing non-spectral projection data (e.g. if the radiation source is controlled to operate in a non-spectral mode). Generally, the non-spectral projection data will include data for a single energy level or energy range. Generally, the spectral projection data and/or spectral volumetric image data will include data generated during an imaging process in which at least two different energies and/or energy ranges are detected and distinguished from one another by the radiation sensitive detector array.

A processing system 118 is configured to receive and process image data from the reconstructor 116. The processing system 118 is a processing system according to one embodiment of the invention. In other embodiments, a processing system may be provided to receive such information from a separate system, e.g. a memory or storage system.

The processing system 118 includes a processor 120 (e.g., a microprocessor, a controller, a central processing unit, etc.) and a computer readable storage medium 122, which excludes non-transitory medium, and includes transitory medium such as a physical memory device, etc. The computer readable storage medium 122 includes instructions 124 for an image processor 126. The processor 120 is configured to execute the instructions 124. The processor 120 may additionally be configured to execute one or more computer readable instructions carried by a carrier wave, a signal and/or other transitory medium. In a variation, the processor 120 and the computer readable storage medium 122 are part of another processing system, which is separate from the processing system 118.

In some examples, the processing system 118 is configured to serve as an operator console. The console 118 may include a human readable output device such as a monitor and an input device such as a keyboard, mouse, etc. Software resident on the console 118 may allow the operator to interact with and/or operate the scanner 102 via a graphical user interface (GUI) or otherwise.

The processing system 118 is configured to process non-spectral CT image data and spectral CT image data. Both types of image data represent a same region of interest of the subject. The non-spectral CT image data is processed (using a machine-learning algorithm) to produce predicted spectral CT image data, i.e. a prediction of what the spectral CT image data contains. The predicted spectral CT image data and the spectral CT image data are processed together to identify any differences. An alert signal is controlled (and preferably output) by the processing system responsive to any identified differences. This approach effectively facilitates identification of the presence of areas in the non-spectral CT image data that fail to contain information of potential clinical importance (i.e. areas that contain information found in the spectral CT image data, but which are absent or unclear in the non-spectral CT image data).

Figure 2:
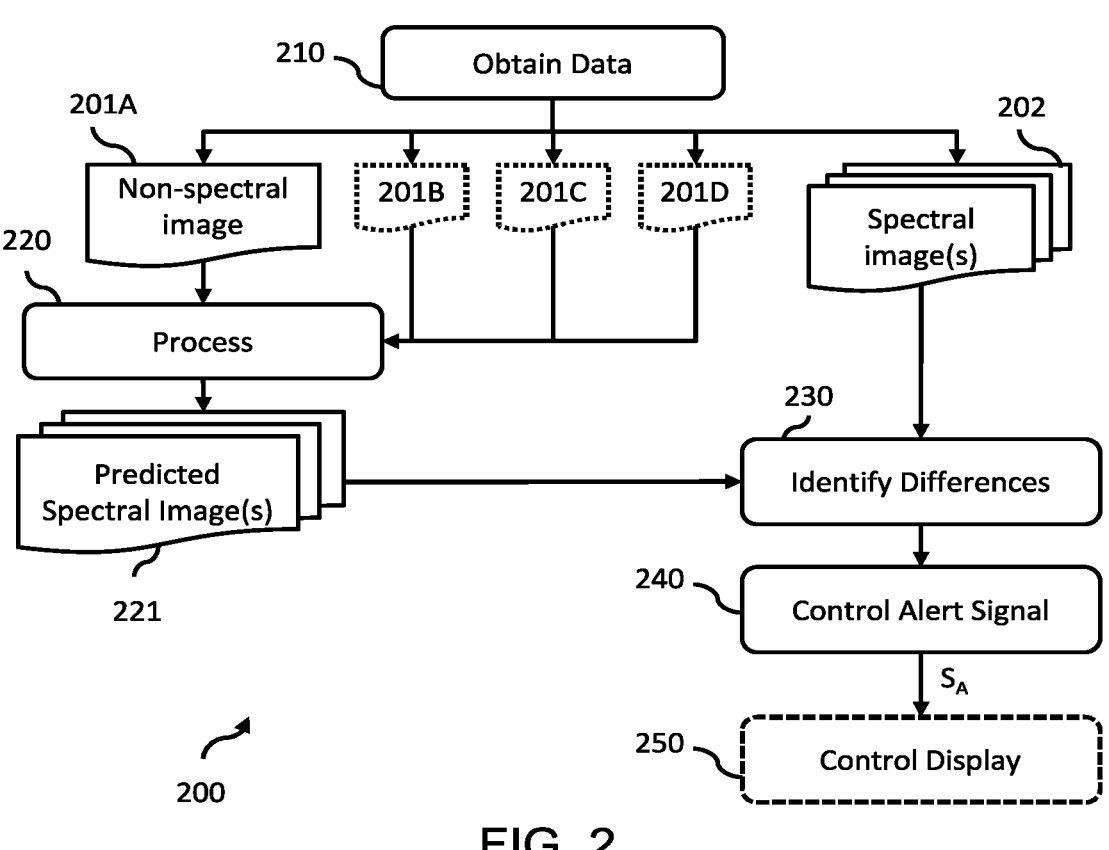
FIG. 2 is a flowchart illustrating a method according to an embodiment.

FIG. 2 is a flowchart illustrating a (computer-implemented) method 200 according to an embodiment of the invention. The method 200 may be performed by a processing system, such as the processing system 118 described with reference to FIG. 1.

The method 200 comprises a step 210 of obtaining non-spectral CT image data 201A and spectral CT image data 202 (which could be relabeled "base spectral CT image data" where appropriate). At the step 210 of obtaining the CT image data both: non-spectral CT image data 201A and spectral CT image data 202 can be obtained during the same CT image acquisition action and can be derivable from the CT image data acquired during said action. Both the non-spectral and spectral CT image data represent a same region of interest of the subject. For instance, both types of obtained image data may represent the entire imaged area of the subject.

The non-spectral and spectral CT image data may comprise one or more 2D or 3D images, i.e. be formed of 2D or 3D image data. Each 2D/3D image may be formed of a plurality of pixels or voxels. Of course, higher dimensionality images could also be used, e.g. where a fourth dimension represents time. In this scenario, the smallest addressable element representing a particular area in space of each high dimensionality image is a "voxel". Of course, each element may contain a plurality of channels or values (e.g. RGB values or the like).

The non-spectral CT image data may be "conventional" CT image data. i.e. image data generated from a single range of X-ray radiation frequencies (e.g. a broadband X-ray radiation). By way of example only, the non-spectral CT image data may comprise one or more non-spectral CT images.

The spectral CT image data may comprise one or more image datasets generated using a spectral imaging approach, such as sCCTA image data, a high-energy image, a low energy image, a photoelectric image, a Compton scatter image, an iodine image, a calcium image, a virtual non-contrast image, a bone image, a soft tissue image, and/or other basis material image. Other forms of content for spectral CT image data will be readily apparent to the person skilled in the art. Thus, the spectral CT image data may comprise one or more spectral CT images.

Step 210 may be performed by an input interface of the processing system. The non-spectral and spectral CT-image data may be obtained from a reconstructor (i.e. that originally generated both types of image data) or a memory/storage system (e.g. that stores image data generated by a reconstructor).

The method 200 than performs a step 220 of processing (at least) the non-spectral CT image data using a machine-learning algorithm to produce predicted spectral CT image data 221. The predicted spectral CT image data 221 attempts to predict the "true" content of the spectral CT image data. Thus, the spectral CT image data 202 represents the "true" spectral CT image data and the predicted spectral CT image data 221 represents the predicted content of this "true" spectral CT image data. Thus, predicted spectral CT image data is a prediction of the (actual) spectral CT image data obtained in step 210.

The machine-learning algorithm thereby attempts to predict the content of the spectral CT image data from (at least) the non-spectral CT image data. Such a machine-learning method has an advantage in that it only needs to be trained on pairs of non-spectral CT image data and corresponding spectral CT image data. Thus, the machine-learning method used in methods of the invention can be trained using an unsupervised learning approach. This eliminates the need to prepare large reliable annotated training data, which is a very challenging, tedious, time-consuming and costly task.

Step 220 may use additional information in processing the non-spectral CT image data to produce the predicted spectral CT image data. Thus, step 220 may comprise processing, using a machine-learning method, the non-spectral CT image data and the additional information in order to generate the predicted spectral CT image data.

The additional information may contain features or information that indicate potential characteristics that would affect spectral CT image data. Thus, the accuracy of the machine-learning methods inference/prediction will be improved through the use of such additional information.

The machine-learning method thereby receives, as input, at least the non-spectral CT image data (and optionally, additional information) and provides, as output, the predicted spectral CT image data. The data received as input may act as input features for the machine-learning method.

In some embodiments, the additional information may comprise input parameter data 201B. The input parameter data defines one or more parameters of the acquisition protocol used, by a CT imaging system, in acquiring the non-spectral CT image data and/or the spectral CT image data. This may comprise, for instance, information or one or more indicators responsive to: a scan type (e.g. single-slice, multi-slice or helical); body part; mA (or milliamperes, being a measure of a current that is provided to an X-ray tube): mAs (or millampere-seconds, being a product of the current provided to the X-ray tube and the amount of time that current is provided to the X-ray tube); kVp (kilovoltage peak); rotation time (of the rotating portion); collimation (of the X-ray beam produced by the X-ray tube); and/or pitch (being a measure of overlap between x-ray beams provided to the subject from a same angle).

In some embodiments. the additional information comprises reconstruction parameter data. The reconstruction parameter data defines one or more parameters of the reconstruction protocol used, by a CT imaging system, to process raw CT data to produce the non-spectral CT image data and/or the spectral CT image data. This may comprise, for instance, information or one or more indicators responsive to: reconstruction filter used; reconstruction algorithm used (e.g. FBP, iDose or IMR); slice thickness; slice increment; matrix size and/or field of view.

In some embodiments, the additional information comprises subject data. The subject data defines one or more parameters of the subject (of the image). The subject data may, for instance, comprise (where the subject is undergoing a clinical observation) information or one or more indicators responsive to: health data of the subject (e.g. medical record information); demographic/personal data of the subject (e.g. age, gender, weight etc.); medical history of the subject (e.g. family history) and so on.

Examples of suitable machine-learning algorithms and approaches will be provided later in this disclosure.

The method 200 further comprises a step 230 of identifying any differences between the spectral CT image data 202 and the predicted spectral CT image data 221. Thus, the spectral CT image data is compared to the predicted spectral CT image data to identify differences or inconsistencies between the two sets of image data.

The differences may be differences that meet one or more predetermined criteria. The differences need not be mathematical differences between the spectral CT image data and the predicted spectral CT image data, but may represent features present in one set of image data, but not in the other set of image data and/or features highly visible (e.g. having a high contrast, e.g. a contrast beyond some predetermined threshold, compared to nearby areas) in one set of image data, but not in the other set of image data.

In particular examples, step 230) may comprise identifying any potentially relevant clinical findings that are present (or readily visible) in the spectral CT image data, but are absent (or not readily visible) in the predicted spectral CT image data. Here, "readily visible" means easily distinguishable to the human eye, e.g. clinical findings that are represented by values in the predicted spectral CT image that are within a predetermined range of values of the surroundings of feature in the predicted spectral CT image data (i.e. are not sufficiently (i.e. with respect to some predetermined threshold) contrasted from the other elements of the predicted spectral CT image).

In particular, any identified differences between the predicted spectral CT image data and the spectral CT image data may represent, or may be processed to identify, areas of predicted/potential clinical relevance. This may comprise, for example, performing one or more grouping steps (e.g. clustering or connected component algorithms or the like) on identified differences and/or filtering operations to identify areas of significance (e.g. significant differences or significantly sized groups of differences).

It is herein recognized that differences between the spectral CT image data and the predicted spectral CT image data may represent areas of the subject that contain clinically important information which is not (clearly) represented in the non-spectral CT image data. In other words, a finding that could not be identified/seen or could barely be seen in the conventional CT images will not be accurately generated by the spectral generative network.

Working examples of step 230) will be provided later in this disclosure.

The method 200 further comprises a step 240 of controlling an alert signal SA responsive to any identified differences. Thus, the content of the alert signal is dependent upon any identified differences. Put another way, step 240) may comprise processing any identified differences to generate the alert signal. Step 240 may comprise outputting the alert signal, e.g. via an output interface of a processing system.

In some examples, step 240) comprises controlling the alert signal to contain or carry one or more indicators of the identified differences. It will be appreciated that the position of 30) differences (between actual and predicted spectral CT image data) can be mapped to corresponding positions of non-spectral CT image data. The alert signal may be controlled to carry one or more indicators of a position of the identified differences with respect to the non-spectral CT image data.

In other examples, step 240) comprises controlling the alert signal to contain an indicator of whether or not any differences have been identified. This information may be used to alert a clinician or other user that differences have been detected, and that closer attention to the CT image data may therefore be required.

In some examples, step 240) comprises controlling the alert signal to contain an indicator of a number of identified differences. This information may be used to alert a clinician or other user as to a scale of possible areas of clinical relevance that are not (readily) visible from the non-spectral CT image data.

In some examples, step 230 or 240 may further comprise identifying one or more parts of the spectral CT image data that contain a representation of any/each identified difference. For instance, if the spectral CT image data is formed of a plurality of spectral CT images, step 240 may comprise identifying, for each identified difference, a spectral CT image that contains a representation of the difference, e.g. the spectral CT image for which a contrast between the area of the spectral CT image representing the difference compared to that areas surroundings is the greatest and/or exceeds some predetermined threshold.

The alert signal may be used to control a user interface, e.g. to provide a user-perceptible output (such as a visual, audio or haptic output) responsive to the alert signal. In some examples, the alert signal may be passed to another processor or processing system for further processing, e.g. to trigger the automatic acquisition of additional CT image data or to flag, e.g. set a flag of, a medical record of the subject. In some examples, the alert signal may carry alert data for storage, e.g. alongside the image data, so that the alert data may trigger the generation of a user-perceptible output during later review of the stored image data.

Steps 220 to 240 may be performed by a processing system, such as the processing system 118 described with reference to FIG. 1.

As previously mentioned, the alert signal may be used to control a user interface. In one example, as illustrated in FIG. 2, the method 200 may comprise a step 250 of controlling a display (i.e. a visual output) responsive to the alert signal. Step 250 may be performed by the processing system or a separate processor (e.g. of the user interface).

By way of example, if the alert signal carries one or more indicators of a position of the identified differences with respect to the non-spectral CT image data, then step 250 may comprise controlling a display to provide a visual representation of the non-spectral CT image data together with a representation of the identified difference(s), e.g. by providing an predetermined graphic or visual indicator to overlay the corresponding location(s) of the non-spectral CT image data.

By way of another example, if the alert signal contains an indicator of whether or not any differences have been identified, step 250) may comprise controlling the display to provide a visual representation (e.g. using different colors) as to whether or not any differences have been identified.

Figure 3:
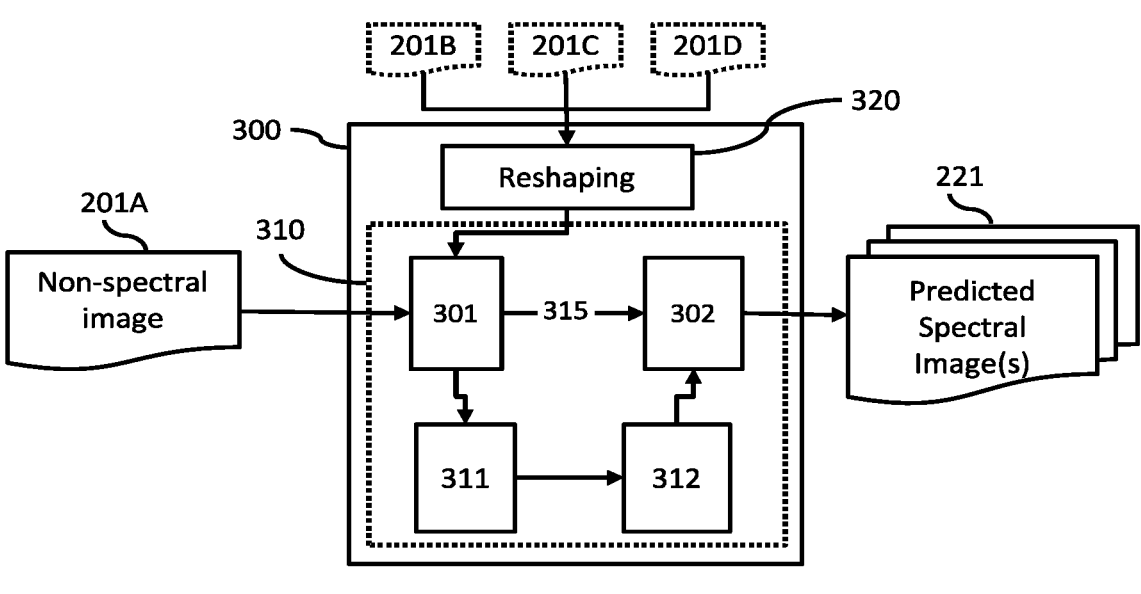
FIG. 3 illustrates a machine-learning method for use in an embodiment.

FIG. 3 illustrates one approach for processing non-spectral CT image data 201A (and optionally additional information) to produce predicted spectral CT image data 221.

A machine-learning algorithm 300) is used to process non-spectral CT image data (and optionally additional information). Thus, the machine-learning algorithm 300 receives, as input, non-spectral CT image data 201A (and optionally additional information 201B, 201C, 201D) and produces predicted non-spectral data 221.

The illustrated machine-learning algorithm 300 is a neural network. The structure of a neural network (or artificial neural network) is inspired by the human brain. Neural networks are comprised of layers 301, 302, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The first layer 301 receives input data, and the final layer 302 provides the output data (e.g. the predicted spectral CT image data).

More specifically, the illustrated machine-learning algorithm operates according to a fully (connected) convolutional (neural) network configuration. In this configuration, input data could be of arbitrary size and the network is able to produce correspondingly sized output data with efficient inference and learning. In some configurations, features across layers of the neural network are fused to define a nonlinear local to-global representation that could be optimized or training end-to-end.

In some examples, rather than using a fully connected convolutional network, a convolutional neural network with a sliding-window configuration could also be also used. Although this process may be more computationally efficient, it is expected to have inferior performance.

The illustrated machine-learning algorithm comprises of the following portions.

A U-net portion 310, which is effectively a U-net network and is formed of a contracting path 311 and an expansive path 312.

In the contracting path, input data (comprising the non-spectral CT image data and optionally the (reshaped) additional information) is encoded using a series of one or more convolution processes (not shown), e.g. at least two convolution processes or at least three convolution processes. Each convolution process comprises applying at least one (e.g. two or more) convolutions (using a filter of size N×N or N×N×N, where N is at least 2, e.g. as least 3). The dimensionality of the filter may be dependent upon (e.g. equal to) the dimensionality of the non-spectral CT image data. Each convolution in the convolution process may be followed by a batch normalization process and an activation function process, e.g. such as that which can be applied by a rectified linear unit (ReLU) or similar. The last convolution of each convolution process is done with stride M (where M>1 and (optionally) M<=N) for down-sampling/downscaling.

In the expansive path, the down-sampled/downscaled convolutional output is decoded using a series of one or more deconvolution processes, e.g. at least two deconvolution processes or at least three deconvolution processes. There may be a same number of deconvolution processes as convolution process, e.g. so that each deconvolution process corresponds (i.e. operates at a same level to) a corresponding deconvolution process. Each deconvolution process comprises applying at least one (e.g. two or more) deconvolutions (using a filter of size N×N or N×N×N, where N is at least 2, e.g. as least 3). Each deconvolution in the deconvolution process may be followed by a batch normalization process and an activation function process, e.g. such as that which can be applied by a rectified linear unit (ReLU) or similar. The last deconvolution of each deconvolution process is done with stride M (where M>1 and (optionally) M<=N) for down-sampling/downscaling.

At the final layer 302 a 1×1×1 convolution may be used to provide the final decoder result, i.e. the output data.

In some examples, one or skip connections 315 may be used to connect layers from the contracting path to corresponding layers of the expansive path. This approach combines better localized, high resolution features from the contracting path combined with the upsampled output of the expansive path, which can produce a more accurate and localized output. The use of skip connections in a neural network architecture will be known to the skilled person. Additional skip connections 315 (not shown) may be used in the neural network.

The number of convolutions performed in each convolution process in the contracting path may be $(2^3)^s.c.$ where s=1.2.3 is the position of the convolution process in the series of convolution processes, e.g. where the first convolution process has value s=1, and c is a network control parameter. Experimental analysis has shown that, for use in the present disclosure, improved performed is achieved in an overcomplete setting, in which c>1.

The number of deconvolutions performed in each deconvolution process may be equal to the number of convolutions performed in the convolution process at the same level as the corresponding deconvolution process.

The neural network 300 may also comprise a reshaping process 320, which may be performed if additional information 201B, 201C, 201D is used to generate the predicted spectral CT image data.

The reshaping process 320 may be configured to preprocess and reshape the additional information for use in the U-net portion 310 of the neural network. This may comprise, for instance, performing two or more fully connected convolutions on the additional information and reshaping the processed information to produce The reshaping may comprise reshaping the processed information to one or more representations having a same size as the non-spectral CT image data. The reshaped information and non-spectral CT image data is then provided to the U-net portion, e.g. in the form of a plurality of channel(s).

Although the machine-learning algorithm is a spectral generative network in the illustrated examples, other forms of machine-learning algorithms could be used.

More generally, a machine-learning algorithm is any self-training algorithm that processes input data in order to produce or predict output data. Here, the input data comprises non-spectral CT image data (and optional additional information) and the output data comprises predicted spectral CT image data.

Other suitable machine-learning algorithms for being employed in the present invention will be apparent to the skilled person. Examples of suitable machine-learning algorithms include decision tree algorithms and artificial neural networks. Other machine-learning algorithms such as logistic regression, support vector machines or Naïve Bayesian models are suitable alternatives.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g. +1%) to the training output data entries.

For example, where the machine-learning algorithm is formed from a neural network, (weightings of) the mathematical operation of each neuron may be modified until the error converges. Known methods of modifying a neural network include gradient descent, backpropagation algorithms and so on.

The training input data entries correspond to sets of example non-spectral CT image data (and optional, corresponding additional information). The training output data entries correspond to spectral CT image data (i.e. representing the same region of interest as the non-spectral CT image data).

One advantage of the proposed approach is that the machine-learning algorithm can be trained in a non-supervised manner. In other words, the machine-learning algorithm does not require professional or clinical input in order to correctly train itself. In this way, generation of an alert signal (effectively identifying the position and/or presence of potential areas of clinical oversight) can be provided in a non-supervised manner. This significantly reduces a difficulty and cost in producing such a mechanism, as well as significantly increasing the amount of available data for training the machine-learning algorithm to be used in the proposed approach, leading to a more accurate machine-learning algorithm.

Figure 4:
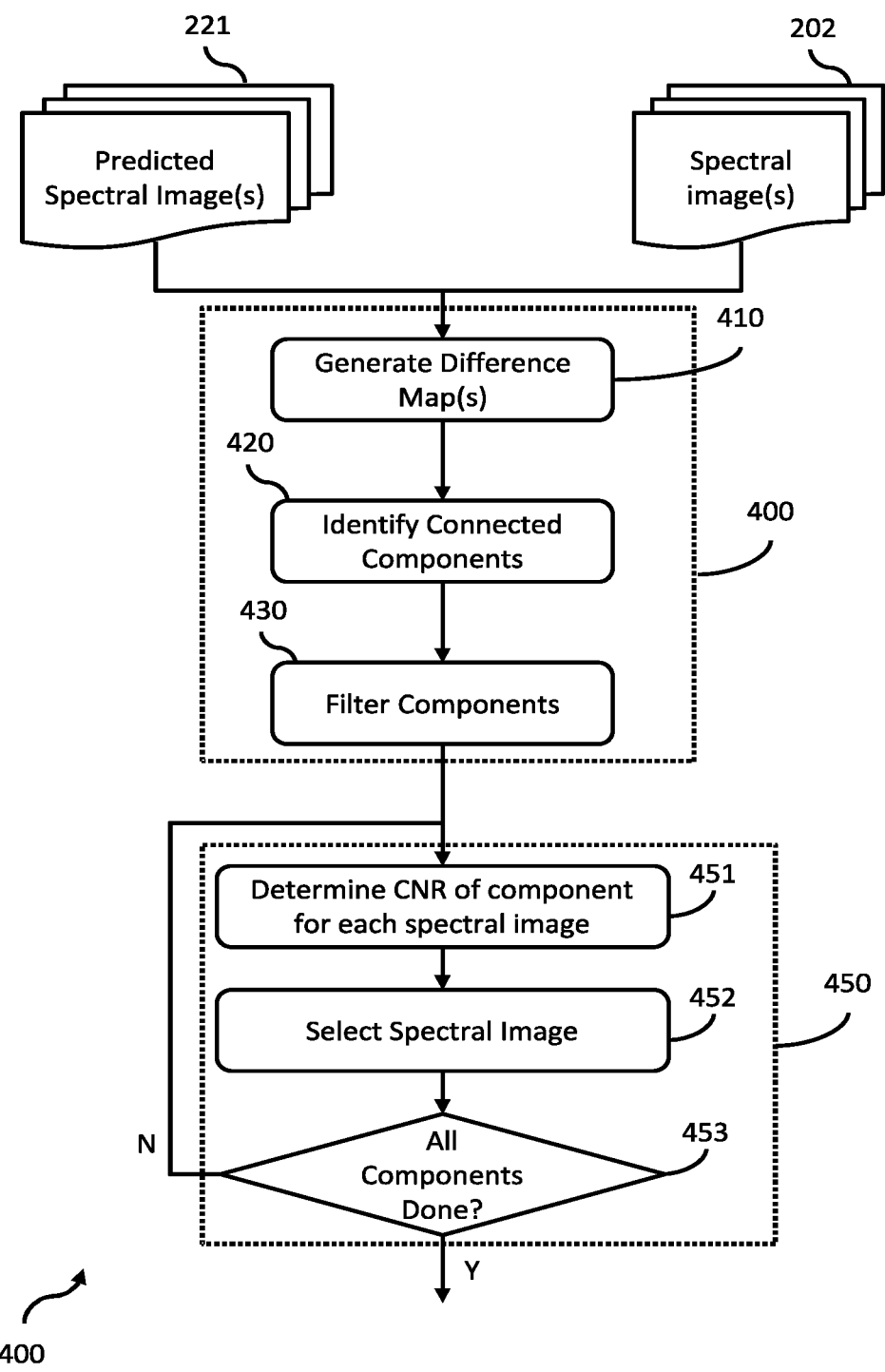
FIG. 4 illustrates a method for use in an embodiment.

FIG. 4 illustrates a method 400 for identifying any differences between spectral CT image data 202 and predicted spectral CT image data 221 (generated/derived from non-spectral CT image data).

Here, the spectral CT image data comprises one or more spectral CT images, and the predicted spectral CT image data comprises a corresponding number of one more predicted spectral CT images. Each predicted spectral CT image corresponds to a spectral CT image (e.g. represents a prediction of the content of the corresponding spectral CT image).

The method 400 effectively identifies, for each of the plurality of spectral CT images, any differences between said CT image and its corresponding predicted CT image. Identified differences may then be processed to identify areas of (predicted) potential clinical importance or relevance (e.g. by applying one or more grouping and/or filtering steps on identified differences). The areas of potential clinical importance or relevance may then be used to control an alert signal, e.g. to draw a clinicians attention to areas of potential clinical importance or to perform additional imaging of the area of potential clinical importance.

The method 400 comprises a step 410 of generating one or more difference maps or difference images by processing the spectral CT image data 202 and the predicted spectral CT image data 221. A map may effectively be difference image data that identifies the presence and/or position of any differences between the CT image data and the predicted spectral CT image data.

Where the spectral CT image data comprises a single CT image, the difference image data may comprise generating a single difference map by directly processing the spectral CT image and the predicted CT image.

Where the spectral CT image data comprises a plurality of spectral CT images, this process 600 may comprise generating a plurality of difference maps, before generating a composite difference map by weighting and/or combining the difference maps together. This effectively identifies the presence and/or position of any differences between any of the spectral CT images and the predicted spectral CT images.

In some examples, the composite difference map is not generated (even when the spectral CT image data comprises a plurality of spectral CT images), so that a plurality of difference maps undergo further processing.

In one example, step 410 comprises calculating a difference image (e.g. for each spectral CT image) by determining, for each pixel of the spectral CT image, a magnitude of a difference between that pixel (value(s)) and the pixel (value(s)) of the predicted spectral CT image. In another example, step 410 comprises calculating a difference image (e.g. for each spectral CT image) using the following function:

$$Map_i = \frac{abs(I_i - \hat{I}_i)}{stdfilt(I_i) + \epsilon} \tag{1}$$

where $Map_i$ represents a pixel i of the difference image Map, $I_i$ represents the spectral CT image I, $\hat{I}_i$ represents a pixel i of the predicted CT image Î, stdfilt(.) represents a standard deviation filtering function and $\epsilon$ represents a small value (e.g. <0.01), which is used to reduce a likelihood that a divide by zero error will occur.

One example standard deviation filtering function is one that process an input image so that a value of each output pixel/voxel is the standard deviation of a neighborhood (e.g. the adjacent 4 pixels around the corresponding input pixel/voxel or the neighboring 8 pixels around the corresponding input pixel/voxel)

In another example, step 410 comprises calculating a difference image (e.g. for each spectral CT image) using the following function:

$$Map_i = \frac{stdfilt(I_i - \hat{I}_i)}{stdfilt(I_i) + \epsilon} \tag{2}$$

In yet another example, step 410 comprises calculating a difference image (e.g. for each spectral CT image) using the following function:

$$Map_i = ncc(I_i, \hat{I}_i) \tag{3}$$

where ncc(.) is a normalized cross-correlation filtering between two images, here: the spectral CT image and the predicted spectral CT image.

In yet another example, step 410 comprises calculating a difference image (e.g. for each spectral CT image) using the following function:

$$Map_i = mi(I_I, \hat{I}_i) \qquad (4)$$

where mi(.) is a mutual information filtering function performed between two images.

Where multiple difference images are generated, e.g. for each spectral CT image, the method 400 may further comprise a process of combining the multiple difference images to produce a composite difference image (e.g. as part of step 410), which may act as the difference image for the rest of the process of 400.

In one example, combining the multiple difference images may comprise simply summing the difference images together, i.e. by adding the values of each corresponding pixel/voxel to one another. In another example, combining the multiple difference images may comprise performed a weighted sum of the difference images. In yet another example, a single one of the difference images may be selected as the "composite difference image", e.g. the difference image that contains the greatest summed pixel value (of all pixels in the difference image).

In another example, the composite difference image is generated by selecting, for each pixel/value of the composite difference image, the maximum value of any of the corresponding (e.g. weighted) pixels/voxels of the difference images. Thus, for a pixel/voxel at position (a,b,c) in the composite difference image, the maximum value of the pixel/voxel at position (a,b,c) in any of the (e.g. weighted) difference images is selected as the value for that pixel/voxel in the composite difference image.

A composite difference image CMap may be calculated using the following equation:

$$CMap = \max_i w_i \cdot Map_i \qquad (5)$$

where max(.) is a maximum function, $w_i$ represents a weight and Map represents a difference map.

The (composite) difference image may then be processed in a step 420 to identify any groups or clusters in the difference image. This process effectively establishes whether there are any clinically relevant areas of the difference image.

Step 420 may comprise, for instance, processing the difference image using a grouping or clustering algorithm to identify any groups or clusters. In some examples, only pixels/voxels having a value above a predetermined threshold (e.g. tr) may form part of a group or cluster. Thus, step 420 may comprise processing the difference image using a thresholding grouping/clustering algorithm.

One example of a suitable grouping/clustering algorithm is a k-means clustering algorithm or a density-based clustering algorithm. Another suitable example is a segmentation algorithm.

Yet another example of a suitable grouping algorithm is a connected components algorithm. A connected component algorithm identifies connected groups of pixels/voxels. The connected component algorithm may be configured to identify connected groups of pixels/voxels that have a value that reaches or exceeds some predetermined threshold value. i.e. is a thresholded connected component algorithm.

The identified groups and/or clusters may then be subject to a filtering process in step 430. Thus, step 430) may comprise filtering or cleaning any identified groups and/or clusters using a filtering process.

The filtering process 430) may comprise, for instance, removing any groups/clusters that are below a predetermined size. By way of example, if a group is a connected component, the filtering process may comprise removing any connected components having a size below some predetermined size (e.g. less than 0.05% or 0.1% or 0.5% or 1% of the total number of pixels of the difference image). This approach reduces the likelihood that noise or clinically irrelevant information is identified.

The filtering process 430 may comprise removing any groups/clusters for which a maximum value contained in the group/cluster is below some second predetermined threshold (e.g. 10% or 20% of the maximum value for the (composite) difference image). This approach increases the likelihood that only significant groups are identified as being of potential clinical relevance.

The filtering process 430) may comprise removing any groups/clusters for which 35 fewer than a predetermined number of pixels/voxels (e.g. 0.05% or 0.1% or 0.5% of the total number of pixels of the difference image) have a value that is above some third predetermined threshold (e.g. 10% or 20% of the maximum value for the (composite) difference image). This approach also increases the likelihood that only significant groups are identified as being of potential clinical relevance.

In some examples, step 410 does not comprise a step of generating a composite difference image. Rather, if multiple difference maps are generated for a respective plurality of spectral CT images, each difference may be processed separately by following the procedure of steps 420 and 430 on each difference map. This approach identifies any suitable groups/clusters in each difference image.

Use of a composite difference map may provide a more efficient mechanism for identifying differences, as the greatest differences contribute to the difference map which is then processed. However, separately processing each difference image may produce more robust/accurate identification of clusters/groups that represent clinically relevant areas (e.g. reduce a likelihood that noise will impact the identification of suitable clusters/groups).

The output of the illustrated process 400 is a set of (zero or more) groups/clusters that each represent an area of potential clinical relevance that is present in the spectral CT image data, but not present or readily apparent in the predicted spectral CT image data. This effectively identifies areas of the non-spectral CT image data that fail to contain or display potentially clinically relevant or important features of the subject that are present or readily apparent in the spectral CT image data.

The set of groups/clusters thereby act as the identified differences between the spectral CT image data and the predicted spectral CT image data. The identified differences thereby act as identified area of potential clinical relevance (that are not present or readily visible in the original non-spectral CT image data).

It will be appreciated that the process 400 effectively identifies a position and size of the area of potential clinical relevance. As the non-spectral CT image data and the spectral CT image data represent a same area of the subject, a position and size of an area in the spectral CT image data can be mapped to a corresponding size and position in the non-spectral CT image data.

The alert signal may be configured to carry an indicator of the size and/or position of each identified area of potential clinical relevance (i.e. each group/cluster). This facilitates identification of areas that require closer or further investigation for performing a clinical assessment.

FIG. 4 also illustrates a process 450) for identifying (for each group/cluster identified in process 400) a spectral CT image that contains or (best) depicts the said group/cluster. This process 450) can be performed where the spectral CT image data contains a plurality of spectral CT images.

In this way, each identified area of potential clinical relevance is mapped to a particular spectral CT image, and in particular, mapped to a clinical image that provides the area of potential clinical relevance in the "cleanest" way.

One approach for carrying out process 450 could be to identify the spectral CT image for which the area that contains the said group/cluster has the lowest contrast-to-noise ratio (CNR).

For instance, process 450 may comprise processing each group/cluster in turn.

A CNR metric is obtained. in step 451 for the position of the group/cluster in the spectral CT image. The spectral CT image having the highest CNR metric at/around this position is then selected in step 452 as the spectral CT image for the group/cluster.

One approach for calculating a CNR metric is to employ the following equation:

$$\widetilde{CNR}(G, S_j, \hat{S}_i) = \text{mean}(\text{abs}(S_j[G] - \hat{S}_i[G]))/(std(\hat{S}_i[G]) + \epsilon) \qquad (6)$$

where G represents the pixel/voxel locations of the group/cluster of pixels/voxels: $S_j$ represents the jth spectral CT image: $\hat{S}_j$ is represents the jth predicted spectral CT image generated by the machine-learning method. In this way $S_j$ [G] and $\hat{S}_j$[G] are the pixel values in G of $S_j$ and $\hat{S}_j$, correspondingly.

Process 450 is repeated until a spectral CT image is identified for each group/cluster identified in process 400.

The alert signal may be (further) controlled to carry, for each identified group/cluster, an identification of the spectral CT image identified by process 450. This information could, for instance, be used to control a display to provide visual representations of the identified spectral CT images and the corresponding locations and/or sizes of the identified groups/clusters with respect to the appropriate spectral CT images.

Thus, the alert signal may be controlled to provide an indicator of, for each identified group/cluster (i.e. each identified difference), an identification of the corresponding spectral CT image (that best/clearly contains a representation of the difference) and a position and/or size and/or shape of the group with respect to that corresponding spectral CT image.

Figure 5:
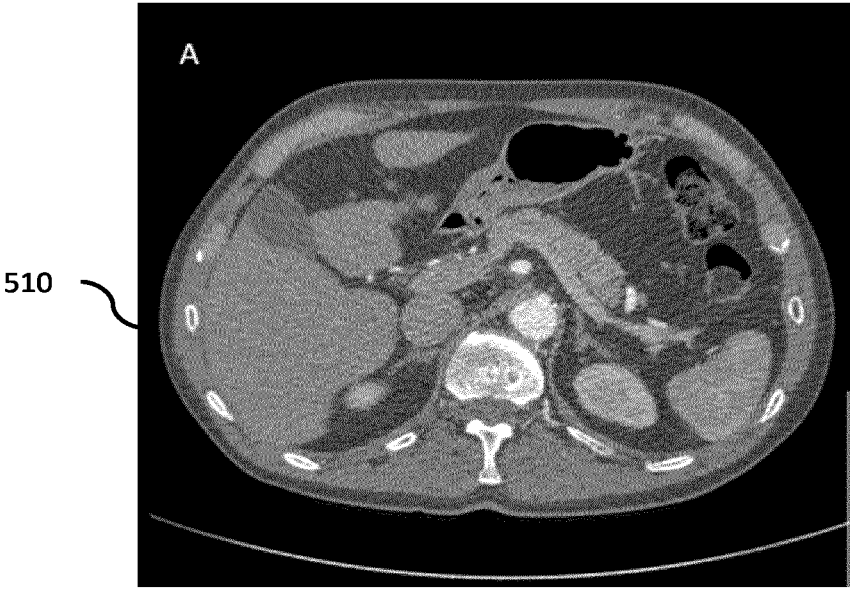
FIG. 5 illustrates exemplary CT images.
Figure 5:
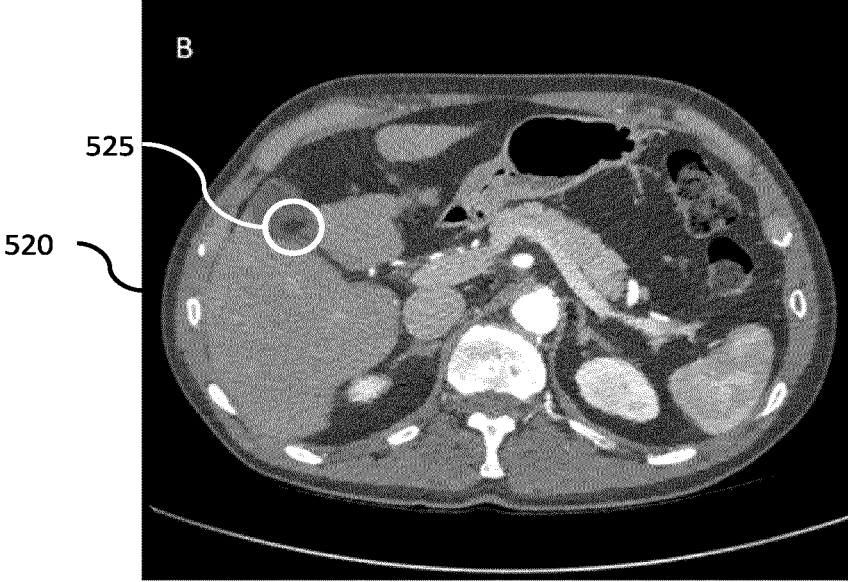

FIG. 5 demonstrates an underlying recognition of the present disclosure. FIG. 5 illustrates two CT images of a same area or region of the subject, containing a representation of the gallbladder (upper-left corner) and the surrounding anatomy.

In particular, FIG. 5 illustrates a first image 510, which is a non-spectral CT image, i.e. a "conventional" CT image obtained using conventional CT image techniques and reconstructions approaches.

FIG. 5 also illustrates a second image 520, which is a spectral CT image, namely a monochromatic 40 keV image. An identified area 525 of the second image contains a gallstone which is not visible in the non-spectral CT image 510.

This example illustrates how potentially clinically relevant features or areas are unidentifiable in the non-spectral CT image, but can be easily identified in the spectral CT image.

FIG. 5 can also be used to understand one example of an embodiment in which a visual representation of a spectral CT image 520 is configured to provide a visual representation of an identified area 525. In this instance, the circle 525 may represent a visual indicator of an identified area.

Figures 6, 7:
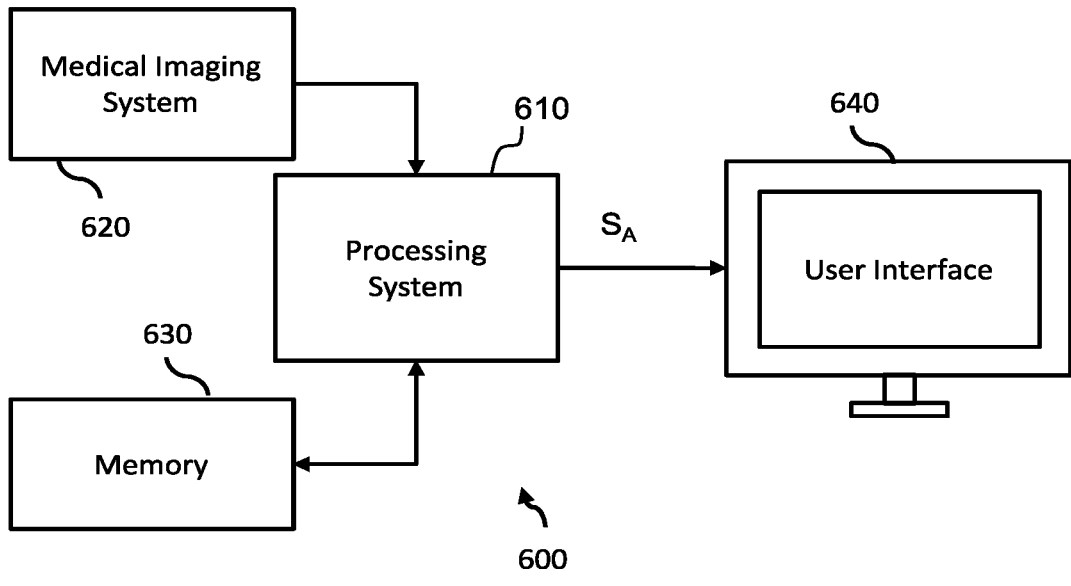
FIG. 6 illustrates another system comprising a processing system according to an embodiment.
FIG. 7 illustrates a processing system according to an embodiment.

FIG. 6 illustrates a system 600 according to an embodiment of the invention.

The system 600 comprises a processing system 610. The processing system 610 is configured for controlling an alert signal SA responsive to differences between spectral CT image data and predicted spectral CT image data.

In particular, the processing system 610 is configured to: obtain non-spectral CT image data and spectral CT image data, each representing a same region of interest of the subject; process the non-spectral CT image data, using a machine-learning algorithm, to produce predicted spectral CT image data, the predicted spectral CT image data being a prediction of the spectral CT image data derived from the non-spectral CT image data; process the spectral CT image data and the predicted spectral CT image data to identify any differences between the spectral CT image data and the predicted spectral CT image data; and control an alert signal responsive to any identified differences.

The processing system 610 may be configured to obtain the non-spectral and/or spectral CT image data from a medical imaging system 620 and/or a memory 630. The processing system may be configured to control a user interface 640, e.g. a display. using the alert signal $S_A$.

The medical imaging system 620, the memory 630 and the user interface 640 form optional components of the system 600.

By way of further example, FIG. 7 illustrates an example of a processing system 70 within which one or more parts of an embodiment may be employed. The processing system 70 provides an example of a suitable processing system for use in previously described embodiments.

Various operations discussed above may utilize the capabilities of the processing system 70. For example, one or more parts of a system for processing non-spectral and spectral CT image data may be incorporated in any element, module, application, and/or component discussed herein. In this regard, it is to be understood that system functional blocks can run on a single computer or may be distributed over several computers and locations (e.g. connected via internet).

The processing system 70 includes, but is not limited to, PCs, workstations, laptops, PDAs, palm devices, servers, storages, and the like. Generally, in terms of hardware architecture, the processing system 70 may include one or more processors 71, memory 72, and one or more I/O devices 77 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 71 is a hardware device for executing software that can be stored in the memory 72. The processor 71 can be virtually any custom made or commercially available processor, a central processing unit (CPU), a digital signal processor (DSP), or an auxiliary processor among several processors associated with the processing system 70, and the processor 71 may be a semiconductor based microprocessor (in the form of a microchip) or a microprocessor.

The memory 72 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 72 may incorporate electronic, magnetic, optical, and/or other types of storage media. Note that the memory 72 can have a distributed architecture, where various components are situated remote from one another, but can be accessed by the processor 71.

The software in the memory 72 may include one or more separate programs, each of which comprises an ordered listing of executable instructions for implementing logical functions. The software in the memory 72 includes a suitable operating system (O/S) 75, compiler 74, source code 73, and one or more applications 76 in accordance with exemplary embodiments. As illustrated, the application 76 comprises numerous functional components for implementing the features and operations of the exemplary embodiments. The application 76 of the processing system 70 may represent various applications, computational units, logic, functional units, processes, operations, virtual entities, and/or modules in accordance with exemplary embodiments, but the application 76 is not meant to be a limitation.

The operating system 75 controls the execution of other computer programs, and provides scheduling, input-output control, file and data management, memory management, and communication control and related services. It is contemplated by the inventors that the application 76 for implementing exemplary embodiments may be applicable on all commercially available operating systems.

Application 76 may be a source program, executable program (object code), script, or any other entity comprising a set of instructions to be performed. When a source program, then the program is usually translated via a compiler (such as the compiler 74), assembler, interpreter, or the like, which may or may not be included within the memory 72, so as to operate properly in connection with the O/S 75. Furthermore, the application 76 can be written as an object oriented programming language, which has classes of data and methods, or a procedure programming language, which has routines, subroutines, and/or functions, for example but not limited to, C. C++, C#, Pascal, BASIC, API calls, HTML, XHTML, XML, ASP scripts, JavaScript, FORTRAN, COBOL, Perl, Java, ADA, .NET, and the like.

The I/O devices 77 may include input devices such as, for example but not limited to, a mouse, keyboard, scanner, microphone, camera, etc. Furthermore, the I/O devices 77 may also include output devices, for example but not limited to a printer, display, etc. Finally, the I/O devices 77 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 77 also include components for communicating over various networks, such as the Internet or intranet.

If the processing system 70 is a PC, workstation, intelligent device or the like, the software in the memory 72 may further include a basic input output system (BIOS) (omitted for simplicity). The BIOS is a set of essential software routines that initialize and test hardware at startup. start the O/S 75, and support the transfer of data among the hardware devices. The BIOS is stored in some type of read-only-memory, such as ROM, PROM, EPROM, EEPROM or the like, so that the BIOS can be executed when the processing system 70 is activated.

When the processing system 70 is in operation, the processor 71 is configured to execute software stored within the memory 72, to communicate data to and from the memory 72, and to generally control operations of the processing system 70 pursuant to the software. The application 76 and the O/S 75 are read, in whole or in part, by the processor 71, perhaps buffered within the processor 71, and then executed.

When the application 76 is implemented in software it should be noted that the application 76 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 76 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The skilled person would be readily capable of developing a processing system for carrying out any herein described method. Thus, each step of the flow chart may represent a different action performed by a processing system, and may be performed by a respective module of the processing system.

Embodiments may therefore make use of a processing system. The processing system can be implemented in numerous ways, with software and/or hardware, to perform the various functions required. A processor is one example of a processing system which employs one or more microprocessors that may be programmed using software (e.g., microcode) to perform the required functions. A processing system may however be implemented with or without employing a processor. and also may be implemented as a combination of dedicated hardware to perform some functions and a processor (e.g., one or more programmed microprocessors and associated circuitry) to perform other functions.

Examples of processing system components that may be employed in various embodiments of the present disclosure include, but are not limited to, conventional microprocessors, application specific integrated circuits (ASICs)., and field-programmable gate arrays (FPGAs). In various implementations, a processor or processing system may be associated with one or more storage media such as volatile and non-volatile computer memory such as RAM, PROM, EPROM, and EEPROM. The storage media may be encoded with one or more programs that, when executed on one or more processors and/or processing systems, perform the required functions. Various storage media may be fixed within a processor or processing system or may be transportable, such that the one or more programs stored thereon can be loaded into a processor or processing system.

It will be understood that disclosed methods are preferably computer-implemented methods. As such, there is also proposed the concept of a computer program comprising code means for implementing any described method when said program is run on a processing system, such as a computer. Thus, different portions, lines or blocks of code of a computer program according to an embodiment may be executed by a processing system or computer to perform any herein described method. In some alternative implementations. the functions noted in the block diagram(s) or flow chart(s) may occur out of the order noted in the figures. For example, two blocks shown in succession may, in fact, be executed substantially concurrently, or the blocks may sometimes be executed in the reverse order. depending upon the functionality involved.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware. but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A computer-implemented method of controlling an alert signal in computed tomography (CT) imaging comprising:

obtaining non-spectral CT image data and spectral CT image data, each representing a same region of interest of a subject;

processing the non-spectral CT image data, using a machine-learning algorithm, to produce predicted spectral CT image data, the predicted spectral CT image data being a prediction of the spectral CT image data derived from the non-spectral CT image data;

processing the spectral CT image data and the predicted spectral CT image data to identify any differences between the spectral CT image data and the predicted spectral CT image data; and controlling an alert signal responsive to any identified differences.

2. The computer-implemented method of claim 1, wherein:

the spectral CT image data comprises a set of one or more spectral CT images;

the predicted CT image data comprises a respective set of one or more predicted spectral CT images, each predicted spectral CT image corresponding to a respective spectral CT image; and identifying any differences between the spectral CT image data and the predicted CT image data comprises, for each spectral CT image, identifying any differences between the spectral CT image and the corresponding predicted spectral CT image.

3. The computer-implemented method of claim 2, wherein identifying any differences between the spectral CT image and the corresponding predicted spectral CT image comprises:

processing the spectral CT image and the corresponding predicted spectral CT image using one or more functions to produce a difference image that identifies a presence and position of differences between the spectral CT image and the corresponding predicted spectral CT image.

4. The computer-implemented method of claim 3, wherein processing the spectral CT image and the corresponding predicted spectral CT image comprises, for each pixel/voxel of the spectral CT image, determining a difference between the pixel/voxel of the spectral CT image and the corresponding pixel/voxel of the predicted spectral CT image.

5. The computer-implemented method of claim 4, wherein processing the spectral CT image and the corresponding predicted spectral CT image comprises:

performing a standard deviation filtering function on the spectral CT image to produce a standard deviation spectral CT image having a same resolution as the spectral CT image; and for each pixel/voxel of the spectral CT image, dividing the determined difference by a value derived from the value of the corresponding pixel/voxel of the standard deviation spectral CT image.

6. The computer-implemented method of claim 3, wherein processing the spectral CT image and the corresponding predicted CT image comprises processing the spectral CT image and the corresponding predicted CT image using a cross-correlation or mutual information function.

7. The computer-implemented method of claim 3, wherein controlling the alert signal comprises controlling the alert signal responsive to the presence and position of differences between the spectral CT image and the corresponding predicted CT image in any difference map.

8. The computer-implemented method of claim 2, wherein the set of one or more spectral CT images comprises a plurality of spectral CT images.

9. The computer-implemented method of claim 8, further comprising identifying, based on any identified differences, one or more of the plurality of spectral CT images that contains a representation of the cause of the identified difference.

10. The computer-implemented method of claim 1, further comprising controlling a user-perceptible output responsive to the alert signal.

11. The computer-implemented method of claim 1, further comprising obtaining input parameter data, the input parameter data defining one or more parameters of the acquisition protocol used, by a CT imaging system, in acquiring the non-spectral CT image data and/or the spectral CT image data, wherein processing the non-spectral CT image data comprises processing the non-spectral CT image data and the input parameter data using the machine-learning algorithm to produce the predicted spectral CT image data.

12. The computer-implemented method of claim 1, further comprising obtaining reconstruction parameter data, the reconstruction parameter data defining one or more parameters of the reconstruction protocol used, by a CT imaging system, to process raw CT data to produce the non-spectral CT image data and/or the spectral CT image data, wherein processing the non-spectral CT image data comprises processing the non-spectral CT image data and the reconstruction parameter data using the machine-learning algorithm to produce the predicted spectral CT image data.

13. The computer-implemented method of claim 1, further comprising obtaining subject data, the subject data defining one or more parameters of the subject, wherein processing the non-spectral CT image data comprises processing the non-spectral CT image data and the subject data using the machine-learning algorithm to produce the predicted spectral CT image data.

14. A system for controlling an alert signal in computed tomography (CT) image processing, the system comprising:

a memory that stores a plurality of instructions; and a processor assembly coupled to the memory and configured to execute the plurality of instructions to:

obtain non-spectral CT image data and spectral CT image data, each representing a same region of interest of a subject;

process the non-spectral CT image data, using a machine-learning algorithm, to produce predicted spectral CT image data, the predicted spectral CT image data being a prediction of the spectral CT image data derived from the non-spectral CT image data;

process the spectral CT image data and the predicted spectral CT image data to identify any differences between the spectral CT image data and the predicted spectral CT image data; and control an alert signal responsive to any identified differences.

15. A non-transitory computer-readable medium for storing executable instructions, which cause a method to be performed to control an alert signal in computed tomography (CT) imaging, the method comprising:

obtaining non-spectral CT image data and spectral CT image data, each representing a same region of interest of a subject;

processing the non-spectral CT image data, using a machine-learning algorithm, to produce predicted spectral CT image data, the predicted spectral CT image data being a prediction of the spectral CT image data derived from the non-spectral CT image data;

processing the spectral CT image data and the predicted spectral CT image data to identify any differences between the spectral CT image data and the predicted spectral CT image data; and controlling an alert signal responsive to any identified differences.

* * * * *